United States Patent
Roberts et al.

(10) Patent No.: US 9,221,725 B2
(45) Date of Patent: Dec. 29, 2015

(54) PRODUCTION OF LUBRICANT BASE OILS FROM BIOMASS

(71) Applicants: Virginia M. Roberts, Weehawken, NJ (US); Michel Daage, Hellertown, PA (US); Paul D. Oldenburg, Cypress, TX (US); Suzzy C. Ho, Princeton, NJ (US); Kun Wang, Bridgewater, NJ (US); Bradley R. Fingland, Annandale, NJ (US)

(72) Inventors: Virginia M. Roberts, Weehawken, NJ (US); Michel Daage, Hellertown, PA (US); Paul D. Oldenburg, Cypress, TX (US); Suzzy C. Ho, Princeton, NJ (US); Kun Wang, Bridgewater, NJ (US); Bradley R. Fingland, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 246 days.

(21) Appl. No.: 13/917,743

(22) Filed: Jun. 14, 2013

(65) Prior Publication Data

US 2014/0024869 A1    Jan. 23, 2014

Related U.S. Application Data

(60) Provisional application No. 61/672,965, filed on Jul. 18, 2012.

(51) Int. Cl.
| | | |
|---|---|---|
| *C07C 1/00* | (2006.01) |
| *C07C 1/207* | (2006.01) |
| *C10G 29/22* | (2006.01) |
| *C10G 3/00* | (2006.01) |
| *C11C 3/00* | (2006.01) |
| *B01J 21/12* | (2006.01) |
| *B01J 23/02* | (2006.01) |
| *B01J 23/10* | (2006.01) |

(52) U.S. Cl.
CPC ............... *C07C 1/2076* (2013.01); *B01J 21/12* (2013.01); *B01J 23/02* (2013.01); *B01J 23/10* (2013.01); *C10G 3/44* (2013.01); *C10G 3/50* (2013.01); *C10G 29/22* (2013.01); *C11C 3/00* (2013.01); *C10G 2300/1014* (2013.01); *C10G 2300/1018* (2013.01); *C10G 2400/10* (2013.01); *Y02E 50/13* (2013.01)

(58) Field of Classification Search
USPC ........................................................ 585/240
See application file for complete search history.

(56) References Cited

U.S. PATENT DOCUMENTS

| 4,992,605 A | 2/1991 | Craig et al. |
| 7,850,841 B2 | 12/2010 | Koivusalmi et al. |
| 7,880,043 B2 | 2/2011 | Chapus et al. |
| 7,888,542 B2 | 2/2011 | Koivusalmi et al. |
| 7,977,517 B2 * | 7/2011 | Cortright et al. ............... 585/240 |
| 8,048,290 B2 | 11/2011 | Knuuttila et al. |
| 8,053,614 B2 | 11/2011 | Aalto et al. |
| 2006/0207166 A1 * | 9/2006 | Herskowitz et al. ............ 44/385 |
| 2008/0302001 A1 | 12/2008 | Koivusalmi et al. |
| 2009/0014354 A1 * | 1/2009 | Knuuttila et al. ............... 208/58 |
| 2011/0015459 A1 | 1/2011 | Aalto et al. |
| 2011/0105814 A1 | 5/2011 | Koivusalmi et al. |
| 2012/0316093 A1 | 12/2012 | Zhan et al. |

FOREIGN PATENT DOCUMENTS

| EP | 457665 B1 | 11/1991 |
| EP | 1681337 B1 | 7/2006 |
| WO | 2007068795 A1 | 6/2007 |
| WO | 2008152199 A1 | 12/2008 |
| WO | 2008152200 A1 | 12/2008 |
| WO | 2011115394 A2 | 9/2011 |
| WO | 2013113976 A1 | 8/2013 |

OTHER PUBLICATIONS

Avelino Corma, et al., "Coupling fatty acids by ketonic decaroxylation using solid catalysts for the direct production of diesel, lubricants, and chemicals," ChemSusChem (2008) 1(8-9), 739-741, Wiley-VCH Verlag GmbH & Co KGaA, Valencia, Spain.
Parida, et al., "Catalytic ketonisation of acetic acid over modified zirconia 1. Effect of alkali-metal cations as promoter", Journal of Molecular Catalysis A: Chemical, Jan. 1, 1999, vol. 139, p. 73-80, Elsevier.
International Search Report with Written Opinion for PCT/US2013/050984 dated Jan. 2, 2014.

* cited by examiner

*Primary Examiner* — Thuan D Dang
(74) *Attorney, Agent, or Firm* — David M. Weisberg

(57) ABSTRACT

Methods are provided for processing glycerides to form lubricant boiling range molecules in a single reactor and/or a single reaction zone. The glycerides are exposed to catalysts that are stable under the conditions present in the reaction zones during conversion of glycerides to fatty ketones via a coupling reaction in the presence of a first catalyst, and the subsequent deoxygenation and isomerization of the ketones in the presence of a second dewaxing catalyst. The glyceride-containing feedstock can further include free fatty acids or fatty acid derivatives that can also be used for formation of ketones and subsequent deoxygenation and isomerization. In some configuration, the processing can occur in a single reaction zone containing mixed beds of the first and second catalyst. Such configurations can be used to control the ratio of diesel boiling range molecules versus lubricant boiling range molecules generated by the methods.

10 Claims, 4 Drawing Sheets

PRODUCTION OF LUBRICANT BASE OILS FROM BIOMASS

CROSS-REFERENCE TO RELATED APPLICATION

This application is a non-provisional application which claims priority to U.S. Ser. No. 61/672,965, filed on Jul. 18, 2012, the entirety of which is incorporated by reference herein.

FIELD OF THE INVENTION

This invention relates to methods for processing biomass to make distillate products.

BACKGROUND OF THE INVENTION

One feedstock source for making renewable distillate products is to use a feedstock that contains triglycerides. Typical triglycerides include a three carbon glycerol backbone that has ester linkages to three longer side chains. Separating the side chains from the glycerol backbone typically results in formation of a fatty acid corresponding to each of the side chains. After separation from the glycerol backbone, many of the fatty acids present in triglycerides can have a chain length that is suitable for use, possibly after further processing, in diesel products such as diesel fuels or diesel fuel additives.

Lubricant base oils are another potential product that can be made from a biomass source. However, triglycerides with fatty acid chain lengths in the lubricant base oil boiling range are currently less common. One option for making a lubricant base oil product from a feed containing fatty acids is to couple two or more fatty acid chains to create molecules with longer chain lengths.

European Patent Application No. EP 0457665 describes performing a condensation reaction on carboxylic acids or polyfunctional compounds such as triglycerides using a catalyst based on an iron-containing mineral, such as bauxite.

U.S. Pat. No. 8,048,290 describes a process for producing branched hydrocarbons. A feedstock derived from a biological starting material, such as a fatty acid or a fatty acid derivative, is subjected to a condensation step to produce hydrocarbons that also contain one or more heteroatoms, such as oxygen or nitrogen. The condensation product is then subject to a combined hydrodefunctionalization and isomerization step. In this combined step, isomerization and heteroatom removal are performed in the same step. Examples of suitable catalysts for performing the combined hydrodefunctionalization and isomerization step include alumina bound ZSM-23 or SAPO-11 with supported Pt as a hydrogenation metal. ZSM-48 is also mentioned as a suitable zeolite.

U.S. Pat. No. 8,053,614 describes a method for producing a base oil. In various options, triglyceride containing feeds are converted to fatty acids or fatty acid alkyl esters. The fatty acids or fatty acid esters are then used to form ketones via a condensation reaction. The ketones are then deoxygenated in a hydrogenation step to form paraffins, which were then isomerized. One or more distillation or separation steps are included at various points in the process of converting the triglyceride containing feed to the isomerized paraffin.

SUMMARY OF THE INVENTION

Methods are provided for processing glycerides to form lubricant boiling range molecules in a single reactor and/or a single reaction zone. The glycerides can be exposed to catalysts that are stable under the conditions present in the reaction zones during conversion of glycerides to fatty ketones via a coupling reaction in the presence of a first catalyst, and the subsequent deoxygenation and isomerization of the ketones in the presence of a second dewaxing catalyst. The glyceride-containing feedstock can further include free fatty acids and/or fatty acid derivatives that can also be used for formation of ketones and subsequent deoxygenation and isomerization. In some configurations, the processing can occur in a single reaction zone containing mixed beds of the first and second catalyst. Such configurations can be used to control the ratio of diesel boiling range molecules versus lubricant boiling range molecules generated by the methods.

In one aspect of the invention, a method for processing a glyceride-containing feedstock is provided. The method includes exposing a feedstock containing glycerides to a catalyst comprising at least about 5 wt % of a rare earth metal salt, an alkali metal salt, an alkaline earth metal salt, or a combination thereof in the presence of hydrogen under effective deoxygenation conditions to form an effluent containing ketones. The amount of ketones in the effluent can be at least about 50% of the weight percentage of the glycerides in the feedstock, e.g., at least about 75% or at least about 90%. In such an aspect, the glycerides in the feedstock can have an average carbon number for side chains in the glycerides, and the average carbon number of ketones in the effluent can be greater than 1.5 times the average carbon number for the side chains, e.g., greater than 1.75 times the average carbon number for the side chains or greater than 1.9 times. At least a portion of the effluent containing ketones can then be exposed, without intermediate separation, to a dewaxing catalyst bound with a hydrothermally stable binder under effective dewaxing conditions to form a deoxygenated effluent, wherein the glycerides in the feedstock can have an average carbon number for side chains in the glycerides, and an average carbon number of the ketones in the effluent can be greater than 1.5 times the average carbon number for the side chains. The feedstock can additionally or alternately contain at least one of free fatty acids and fatty acid derivatives. Optionally, when the combined weight percentage of free fatty acids and/or fatty acid derivatives is at least about 10% of the combined weight of glycerides, free fatty acids, and fatty acid derivatives, the average carbon number of the ketones in the effluent can be greater than about 1.5 times a weighted average carbon number for the side chains of the glycerides and the chains of the free fatty acids and/or fatty acid derivatives.

In another aspect of the invention, a method for processing a glyceride-containing feedstock is provided. The method includes exposing a feedstock containing at least 10 wt % glycerides to a catalyst mixture comprising a dewaxing catalyst bound with a hydrothermally stable binder and a catalyst comprising at least about 5 wt % of a rare earth metal salt, alkali metal salt, alkaline earth metal salt, or a combination thereof in the presence of hydrogen under effective deoxygenation conditions, the effective deoxygenation conditions including a temperature of at least about 300° C., to form a deoxygenated effluent. The glycerides in the feedstock can have an average carbon number for side chains in the glycerides, and at least 1 wt % of the deoxygenated effluent can comprise lubricant boiling range molecules derived from the glycerides in the feedstock, with the lubricant boiling range molecules having a number of carbon atoms greater than 1.5 times the average carbon number for the glyceride side chains. The feedstock can additionally or alternately contain at least one of free fatty acids and fatty acid derivatives.

Optionally, when the combined weight percentage of free fatty acids and fatty acid derivatives is at least about 10% of the combined weight of glycerides, free fatty acids, and fatty acid derivatives, the average carbon number of the ketones in the effluent can be greater than about 1.5 times a weighted average carbon number for the side chains of the glycerides and the chains of the free fatty acids and/or fatty acid derivatives.

In still another aspect of the invention, a method for processing a glyceride-containing feedstock is provided. The method includes exposing a glyceride-containing feedstock containing at least 25 wt % of a combined weight of glycerides, free fatty acids, and fatty acid derivatives to a catalyst mixture in the presence of hydrogen under effective deoxygenation conditions to form a deoxygenated effluent. The effective deoxygenation conditions can advantageously include a temperature of at least about 300° C. Preferably, the fatty acid derivatives are fatty acid esters or fatty acid amides. The catalyst mixture can comprise a) a dewaxing catalyst comprising ZSM-48, ZSM-23, or a combination thereof, the dewaxing catalyst being bound with a hydrothermally stable binder comprising zirconium oxide, titanium oxide, cerium oxide, or a combination thereof, and b) a catalyst comprising at least about 5 wt % of a rare earth metal salt, alkali metal salt, alkaline earth metal salt, or a combination thereof on a support comprising zirconium oxide, titanium oxide, cerium oxide, or a combination thereof. The glycerides, free fatty acids, and fatty acid derivatives in the feedstock have a weighted average carbon number for the fatty acid chains and the side chains in the glycerides. At least 1 wt % of the deoxygenated effluent comprises lubricant boiling range molecules derived from the free fatty acids, fatty acid derivatives, and glycerides in the feedstock. These lubricant boiling range molecules can have an average number of carbon atoms greater than 1.5 times the weighted average carbon number for the side chains of the glycerides and the fatty acid chains of the free fatty acids and/or fatty acid derivatives.

DETAILED DESCRIPTION OF THE PREFERRED EMBODIMENTS

Figure 1:
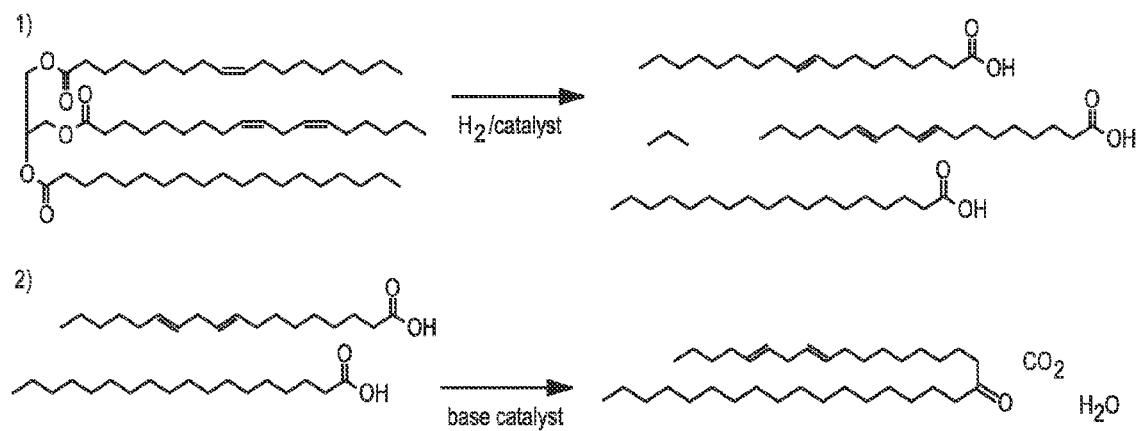
FIG. 1 shows a conventional reaction sequence for converting a triglyceride to a ketone.

In various embodiments, systems and methods are provided for processing a feed containing glycerides (such as triglycerides) in a single bed and/or single reactor configuration to form distillate boiling range molecules. The methods can allow for conversion of glyceride molecules to isomerized lubricant and diesel boiling range products without an intermediate separation. The methods can be enabled by use of a dewaxing catalyst having enhanced activity and tolerance of the subcritical water generated during deoxygenation of a triglyceride-containing feed. In various aspects, the methods can be additionally or alternately suitable for conversion of feeds containing free fatty acids and/or fatty acid derivatives such as fatty acid esters and/or fatty acid amides.

One potential use for a glyceride-containing feed is to combine two or more fatty acid side chains of the glycerides to form a larger molecule. For example, the side chains of a triglyceride can typically be between 14 to 22 carbons long, making the side chains more suitable for use as a diesel fuel product. By combining two side chains to form a larger molecule, the side chains can be converted to molecules suitable in a lubricant base oil boiling range. For example, a coupling reaction can be used to combine two carboxylic acids to form a ketone. Additionally or alternately, fatty acid chains from free fatty acids and/or fatty acid derivatives can participate in such coupling reactions, with fatty acid side chains from glycerides and/or with fatty acid chains from other free fatty acids and/or fatty acid derivatives.

Processing of biomass feeds, however, can pose difficulties for refinery processes, e.g., due to the water generated during deoxygenation of a feed. Conventional methods can typically involve an initial process step for converting glycerides to another form, such as by separating fatty acid side chains in a triglyceride from the glycerol backbone. While various refinery processes can be capable of performing this conversion, the water and other by-products of the reaction can pose difficulties for downstream processes. As a result, a deoxygenation step can often be performed as an initial process in a separate reactor, which could allow any water and heat generated during deoxygenation to be removed in a controlled manner. While this can avoid difficulties due to excess water production, isolating process steps in separate reactors can usually require additional equipment and processing costs.

The cost of converting a glyceride-containing feed into lubricant boiling range molecules can be reduced by selecting reaction catalysts effective for performing the conversion in a single reactor while also being stable in the resulting reaction environment. A first catalyst can be a metallic catalyst effective for catalyzing a condensation reaction to form ketones. A second catalyst can be a dewaxing catalyst tolerant of the water generated during the deoxygenation and coupling reactions for forming the ketones. Depending on the desired product mix, the two catalysts can be used in a stacked bed arrangement, or the catalysts can be mixed within a catalyst bed. In a stacked bed arrangement, the effluent from exposing the catalyst to one or more catalyst beds of the first catalyst can be cascaded or otherwise passed into a catalyst bed containing the second catalyst, e.g., without intermediate separation of gas phase products.

Feedstocks

In the discussion below, a feed derived from a biological source (i.e., a biocomponent feed(stock)) refers to a feedstock derived from a biological raw material component, such as vegetable fats/oils or animal fats/oils, fish oils, pyrolysis oils, and algae lipids/oils, as well as components of such materials, and in some embodiments can specifically include one or more types of lipid compounds. Lipid compounds are typically biological compounds that are insoluble in water, but soluble in nonpolar (or fat) solvents. Non-limiting examples of such solvents include alcohols, ethers, chloroform, alkyl acetates, benzene, and combinations thereof.

Major classes of lipids can include, but are not necessarily limited to, fatty acids, glycerol-derived lipids (including fats, oils and phospholipids), sphingosine-derived lipids (including ceramides, cerebrosides, gangliosides, and sphingomyelins), steroids and their derivatives, terpenes and their derivatives, fat-soluble vitamins, certain aromatic compounds, and long-chain alcohols and waxes.

In living organisms, lipids generally serve as the basis for cell membranes and as a form of fuel storage. Lipids can also be found conjugated with proteins or carbohydrates, such as in the form of lipoproteins and lipopolysaccharides.

Examples of vegetable oils that can be used in accordance with this invention can include, but are not limited to, rapeseed (canola) oil, soybean oil, coconut oil, sunflower oil, palm oil, palm kernel oil, peanut oil, linseed oil, tall oil, corn oil, castor oil, jatropha oil, jojoba oil, olive oil, flaxseed oil, camelina oil, safflower oil, babassu oil, tallow oil, rice bran oil, and the like, and combinations thereof.

Vegetable oils as referred to herein can also include processed vegetable oil material as a portion of the feedstock. Non-limiting examples of processed vegetable oil material include fatty acids and/or fatty acid alkyl esters. Alkyl esters can typically include $C_1$-$C_5$ alkyl esters. One or more of methyl, ethyl, and propyl esters can be preferred.

Examples of animal fats that can be used in accordance with the invention include, but are not limited to, beef fat (tallow), hog fat (lard), turkey fat, fish fat/oil, chicken fat, and the like, and combinations thereof. The animal fats can be obtained from any suitable source including restaurants and meat production facilities.

Animal fats as referred to herein also include processed animal fat material. Non-limiting examples of processed animal fat material include fatty acids and/or fatty acid alkyl esters. Alkyl esters can typically include $C_1$-$C_5$ alkyl esters. One or more of methyl, ethyl, and propyl esters can be preferred.

Algae oils or lipids can typically be contained in algae in the form of membrane components, storage products, and/or metabolites. Certain algal strains, particularly microalgae such as diatoms and cyanobacteria, can contain proportionally high levels of lipids. Algal sources for the algae oils can contain varying amounts, e.g., from 2 wt % to 40 wt %, of lipids based on total weight of the biomass itself.

Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

Other biocomponent feeds usable in the present invention can include any of those which comprise primarily triglycerides, diglycerides, monoglycerides, and free fatty acids (FFAs). The triglycerides, diglycerides, monoglycerides, and FFAs typically contain aliphatic hydrocarbon chains in their structure having from 8 to 36 carbons, for example from 10 to 26 carbons or from 14 to 22 carbons. Types of triglycerides can be determined according to their fatty acid constituents. The fatty acid constituents can be readily determined using Gas Chromatography (GC) analysis. This analysis involves extracting the fat or oil, saponifying (hydrolyzing) the fat or oil, preparing an alkyl (e.g., methyl) ester of the saponified fat or oil, and determining the type of (methyl) ester using GC analysis. In one embodiment, a majority (i.e., greater than 50%) of the glyceride present in the lipid material can be comprised of $C_{10}$ to $C_{26}$ fatty acid constituents, based on total glyceride present in the lipid material. Further, a glyceride is a molecule having a structure identical to the hydrolysis reaction product of glycerol and one, two, or three fatty acids. Thus, although a glyceride is described herein as being comprised of one or more fatty acids, it should be understood that the fatty acid component does not necessarily contain a carboxylic acid hydrogen. If glycerides are present, a majority of glycerides present in the biocomponent feed can preferably be comprised of $C_{12}$ to $C_{18}$ fatty acid constituents, based on total triglyceride content. Other types of feed that are derived from biological raw material components can include fatty acid esters, such as fatty acid alkyl esters (e.g., FAME and/or FAEE) and/or fatty acid amides.

One method for characterizing the glycerides in a feedstock is based on the number of carbons in the side chains. While some feedstocks may have consistent numbers of carbons in each side chain, such as in a tristearin feedstock, many types of glycerides will have variations in chain length between molecules and even within molecules. In order to characterize these variations, the average number of carbons per side chain in the glycerides can be determined. For example, consider a feedstock containing glycerides in the form of triglycerides. By definition a triglyceride contains three side chains. Each side chain contains a number of carbons, as mentioned above. By averaging the number of carbons in each side chain for the triglycerides in a feedstock, an average side chain length for all triglycerides can be determined. The average number of carbons (also referred to as average carbon number) per side chain in the feedstock can be used as a comparative value for characterizing products. For example, the average number of carbons per side chain in the feedstock can be compared with the average number of carbons in ketones and/or isomerized hydrocarbons generated by converting and/or isomerizing the glyceride-containing feedstock. More generally, the average number of carbons in all side chains for all types of glycerides in a feedstock can be used in place of the average number of carbons per side chain in only the triglycerides in a feedstock. Still more generally, a weighted average can be determined for chains in free fatty acids, fatty acid derivatives, and side chains of glycerides.

In various aspects, the production of ketones and corresponding deoxygenated products can be based on processing of glycerides (such as monoacylglycerides, diacylglycerides, and/or triacylglycerides), free fatty acids, and/or fatty acid derivatives within the biocomponent feed. Thus, the presence of at least some glycerides, free fatty acids, and/or fatty acid derivatives within the biocomponent portion of a feed can be desirable. In some aspects, the presence of at least some glycerides in the biocomponent portion of the feed can be preferred, in order to take advantage of the ability to start with a glyceride-containing feed and to produce desirable diesel and/or lubricant boiling range molecules in a single process. The feed can include at least about 10 wt % of feed based on a biocomponent source(s), for example at least about 25 wt %. Preferably, the biocomponent portion of the feed can be at least about 50 wt %, for example at least about 75 wt %, at least about 90 wt %, or at least about 95 wt %. Such higher amounts of feed from a biocomponent source can provide an advantage based on the greater amount of renewable material. Additionally or alternately, the feed can be entirely a feed from a biocomponent source, or the feed can include about 99 wt % or less of a feed based on a biocomponent source, for example about 95 wt % or less, about 90 wt % or less, about 75 wt % or less, or about 50 wt % or less.

Higher amounts of feed from a biocomponent source can provide an advantage based on the greater amount of renewable material, as well as potentially including a greater amount of glycerides. Feeds with lower amounts of biocomponent materials may have other processing advantages. Such advantages can include improved flow characteristics within a reaction system, as biocomponent feeds often have a relatively high viscosity compared to conventional diesel or lubricant feeds in a refinery. Additionally or alternately, deoxygenation of a biocomponent feed can typically generate a substantial amount of heat due to formation of highly favorable products from a free energy standpoint, such as $H_2O$ and $CO_2$. For a typical catalyst bed with a bed length of 25-30 feet (about 9-10 meters), it can be preferable to have a temperature increase across the bed of 100° F. (55° C.) or less. If deoxygenation of a biocomponent feed with a relatively high oxygen content is performed using a sufficiently reactive catalyst, an exotherm of greater than 100° F. across the catalyst bed can be generated. Blending a biocomponent feed with a portion that does not contain oxygen can reduce the exotherm generated across a catalyst bed used for performing deoxygenation.

The advantages of increased mineral feed content can be largely due to dilution of the biocomponent feed, as the processing conditions effective for deoxygenation of a biocomponent feed can have a low or minimal impact on a typical hydroprocessed mineral feed. Therefore, while the deoxygenation conditions can be effective for deoxygenation of biocomponent feeds at a variety of blend ratios with mineral feeds, it can be preferable to have at least about 75 wt % of the feed from a biocomponent source, for example at least about 90 wt % or at least about 95 wt %.

One option for increasing the biocomponent content of a feed while retaining some of the benefits of adding a feed with reduced oxygen content can be to use recycled product from processing of biocomponent feed as a diluent. A recycled product from processing a biocomponent feed is still derived from a biocomponent source, and therefore such a recycled product is counted as a feed portion from a biocomponent source. Thus, a feed containing 60% biocomponent feed that has not been processed and 40% of a recycled product from processing of the biocomponent feed would be considered as a feed that includes 100% of feed from a biocomponent source. As an example, at least a portion of the product from processing of a biocomponent feed can be a diesel boiling range product. Such a recycled diesel boiling range product can advantageously be deoxygenated, and therefore incorporation of the recycled diesel boiling range product in the feed can advantageously reduce the exotherm generated during deoxygenation. Adding a recycled diesel boiling range product is also likely to improve the cold flow properties of a biocomponent feed. More generally, any convenient product from processing of a biocomponent feed can be recycled for blending with the biocomponent feed in order to improve the cold flow properties and/or to reduce the oxygen content of the input flow to a deoxygenation process. If a recycled product flow is added to the input to a deoxygenation process, the amount of recycled product can correspond to at least about 10 wt % of the feed to the deoxygenation process, for example at least about 25 wt % or at least about 40 wt %. Additionally or alternately, the amount of recycled product in a feed can be about 60 wt % or less, for example about 50 wt % or less, 40 wt % or less, or about 25 wt % or less.

While feed dilution can be used to control the exotherm generated across a catalyst bed used for deoxygenation, it is noted that some processing options can additionally or alternately impact the exotherm. One alternative can be to use a less reactive catalyst, so that a larger amount of catalyst can be needed at a given liquid hourly space velocity (LHSV) in order to deoxygenate a feed to a desired level. An additional or alternate option can be to reduce the amount of hydrogen provided for the deoxygenation process. Still another additional or alternate option could be to introduce additional features into a reactor to assist in cooling and/or transporting heat away from a deoxygenation catalyst bed. In combination with selecting an appropriate amount of product recycle and/ or blending of another non-oxygenated feed, a desired combination of a flow characteristics and heat generation during deoxygenation can be achieved.

With regard to glyceride content, the feedstock can include at least about 10 wt % glycerides, for example at least about 25 wt %, preferably at least about 40 wt %, at least about 60 wt %, or at least about 80 wt %. Additionally or alternately, the feed can be composed entirely of glycerides, or the glyceride content of the feed can be about 99 wt % or less, for example about 95 wt % or less, about 90 wt % or less, about 75 wt % or less, or about 50 wt % or less. The glycerides can be monoglycerides, diglycerides, and/or triglycerides. Preferably, the glycerides are triglycerides or a mixture of glycerides that includes triglycerides. The methods described herein can be suitable for conversion of glycerides to lubricant and diesel products in a single reactor, so higher contents of glycerides can be preferred. However, to the degree that a recycle loop is used to improve the feed flow properties or reduce the reaction exotherm across catalyst beds, lower glyceride contents may be beneficial. Optionally, a portion of the glyceride content in the feedstock can be replaced by free fatty acid content and/or fatty acid derivative content. In such an optional aspect, the above weight percentages can refer to the combined weight percentage of glycerides, free fatty acids, and/or fatty acid derivatives in the feedstock.

Biocomponent based diesel boiling range feedstreams can have a wide range of nitrogen and/or sulfur contents. For example, a biocomponent based feedstream based on a vegetable oil source can contain up to about 300 wppm nitrogen. In contrast, a biomass based feedstream containing whole or ruptured algae can sometimes include a higher nitrogen content. Depending on the type of algae, the nitrogen content of an algae based feedstream can be at least about 2 wt %, for example at least about 3 wt %, at least about 5 wt %, or at least about 10 wt %, and algae with still higher nitrogen contents are known. The sulfur content of a biocomponent feed can also vary. In some embodiments, the sulfur content can be about 500 wppm or less, for example about 100 wppm or less, about 50 wppm or less, or about 10 wppm or less.

Aside from nitrogen and sulfur, oxygen can be another heteroatom component in biocomponent based feeds. A biocomponent diesel boiling range feedstream based on a vegetable oil, prior to hydrotreatment, can include up to about 10 wt % oxygen, for example up to about 12 wt % or up to about 14 wt %. Additionally or alternately, such a biocomponent diesel boiling range feedstream can include at least about 1 wt % oxygen, for example at least about 2 wt %, at least about 3 wt %, at least about 4 wt %, at least about 5 wt %, at least about 6 wt %, or at least about 8 wt %. Further additionally or alternately, a biocomponent feedstream, prior to hydrotreatment, can include an olefin content of at least about 3 wt %, for example at least about 5 wt % or at least about 10 wt %.

A mineral feedstock refers to a conventional (e.g., non-biocomponent) feedstock, typically derived from crude oil and that has optionally been subjected to one or more separation and/or other refining processes. When mineral feedstock is present, in one preferred embodiment, the mineral feedstock can be a petroleum feedstock boiling in the diesel range or above. Examples of suitable mineral feedstocks can include, but are not limited to, virgin distillates, hydrotreated virgin distillates, kerosene, diesel boiling range feeds (such as hydrotreated diesel boiling range feeds), light cycle oils, atmospheric gas oils, and the like, and combinations thereof.

Mineral feedstocks for blending with a biocomponent feedstock can be relatively free of nitrogen (such as a previously hydrotreated feedstock) or can have a nitrogen content from about 1 wppm to about 2000 wppm nitrogen, for example from about 50 wppm to about 1500 wppm or from about 75 to about 1000 wppm. In some embodiments, when the mineral feedstock is present, it can have a sulfur content from about 1 wppm to about 10,000 wppm sulfur, for example from about 10 wppm to about 5,000 wppm or from about 100 wppm to about 2,500 wppm.

When present, a mineral feedstock for blending with a biocomponent feedstock can preferably be a mineral feedstock with a relatively low sulfur content, such as a hydrotreated mineral feedstock. Using a mineral feedstock for blending that contains a sufficiently low sulfur content can allow a resulting product to meet a desired sulfur specification without requiring a subsequent hydrotreatment under conditions that saturate olefins. Such preferred feedstocks can be relatively free of sulfur, or can have a sulfur content from about 1 wppm to about 500 wppm, such as from about 10 wppm to about 200 wppm of sulfur or from about 20 wppm to about 100 wppm of sulfur. Additionally or alternately, the combined (biocomponent plus mineral) feedstock can have a sulfur content of at least about 5 wppm, for example at least about 10 wppm, at least about 25 wppm, or at least about 100 wppm. Further additionally or alternately, the combined feedstock can have a sulfur content of about 500 wppm or less, about 100 wppm or less, or about 50 wppm or less. Still further additionally or alternately, the nitrogen content of the combined feedstock can be about 1000 wppm or less, for example about 500 wppm or less, about 100 wppm or less, about 50 wppm or less, about 30 wppm or less, about 20 wppm or less, or about 10 wppm or less.

The content of sulfur, nitrogen, oxygen, and olefins in a feedstock created by blending two or more feedstocks can typically be determined using a weighted average based on the blended feeds. For example, a mineral feed and a biocomponent feed can be blended in a ratio of 80 wt % mineral feed and 20 wt % biocomponent feed. If the mineral feed has a sulfur content of about 1000 wppm, and the biocomponent feed has a sulfur content of about 10 wppm, the resulting blended feed could be expected to have a sulfur content of about 802 wppm.

The boiling range for biocomponent feedstreams suitable for use according to the invention can vary depending on the nature of the biocomponent source. Biocomponent feedstreams with final boiling points up to about 1000° F. (538° C.) may be suitable for use, as the triglycerides within a biocomponent feedstream will have a higher boiling point than the boiling point of the individual chains attached to the glycerol backbone. Mineral feedstreams suitable for use as a blending component tend to boil within the range of about 215° F. (about 102° C.) to about 800° F. (about 427° C.). Preferably, a mineral feedstream has an initial boiling point of at least about 215° F. (about 102° C.), for example at least about 250° F. (about 121° C.), at least about 275° F. (about 135° C.), at least about 300° F. (about 149° C.), at least about 325° F. (about 163° C.), at least about 350° F. (about 177° C.), at least about 400° F. (about 204° C.), or at least about 451° F. (about 233° C.). Preferably, a mineral feedstream has a final boiling point of about 800° F. (about 427° C.) or less, or about 750° F. (about 399° C.) or less. Additionally or alternately, a feedstock can be characterized by the boiling point required to boil a specified percentage of the feed. For example, the temperature required to boil at least 5 wt % of a feed is referred to as a "T5" boiling point. A suitable mineral (petroleum) feedstock can have a T5 boiling point of at least about 230° F. (about 110° C.), for example at least about 250° F. (about 121° C.) or at least about 275° F. (about 135° C.). Further additionally or alternately, the mineral (petroleum) feedstock can have a T95 boiling point of about 775° F. (about 418° C.) or less, for example about 750° F. (about 399° C.) or less or about 725° F. (about 385° C.) or less. In another embodiment, the diesel boiling range feedstream can also include kerosene range compounds to provide a feedstream with a boiling range from about 250° F. (about 121° C.) to about 800° F. (about 427° C.).

With regard to product effluents, deoxygenated effluents, or converted effluents, diesel boiling range streams are defined herein as streams with a T95 boiling point of about 400° C. or less, while lubricant boiling range streams are defined herein as streams with a T5 boiling point above about 400° C.

Reactions for Oxygen Removal

Oxygen removal during hydroprocessing of a feedstock typically occurs via at least one of three reaction pathways. One potential reaction pathway is hydrodeoxygenation. In a hydrodeoxygenation reaction, oxygen is typically removed from feed molecule as water. The carbon chain for the feed molecule tends to remain intact after a typical hydrodeoxygenation reaction. Water is typically a contaminant that can potentially contribute to deactivation of some conventional dewaxing catalysts, such as conventional alumina bound zeolite catalysts. However, by itself water typically does not lead to corrosion within a reaction system. Additionally, removing oxygen as water tends to maintain the chain length of a feed molecule. Maintaining the chain length of molecules intended for use as a fuel or fuel blending product is usually beneficial, as it means that a greater percentage of the carbon from the feed can be incorporated into the final fuel product.

Another potential reaction is (hydro)decarboxylation, which includes removing oxygen by forming $CO_2$ from bio-feeds. This $CO_2$ tends to form carbonic acid when combined with water. Carbonic acid corrosion may require metallurgical upgrades to carbon steel in downstream equipment, particularly fin fans, heat exchangers, and other locations where liquid water will be present prior to an amine scrubbing system or other system for removing $CO_2$.

Another potential reaction is (hydro)decarbonylation, which includes removing oxygen by forming CO from biofeeds. CO is a known inhibitor for hydrodesulfurization. For example, 1000 ppm CO can deactivate a conventional CoMo supported catalyst by at least 10%. CO is also typically not removed in appreciable quantities by conventional amine scrubbing systems. As such, CO can build up through gas recycle and can be cascaded to downstream hydrotreatment, dewaxing, and/or hydrofinishing stages. As a result, removing oxygen from a biocomponent feed as CO may require the use of pressure swing adsorbers (including rapid cycle pressure swing adsorbers) or other gas cleaning equipment in order to remove CO from a reaction system.

Depending on the conditions present in a reactor, the relative amounts of CO and $CO_2$ in a reactor can be modified by the water gas shift reaction. The water gas shift reaction is an equilibrium reaction that can convert $CO_2$ and $H_2$ into CO and $H_2O$. Due to the water gas shift reaction, the amount of decarbonylation and decarboxylation may not be clear, due to conversion from one form of carbon oxide to another. Hydrodeoxygenation can be distinguished at least in part from decarbonylation and decarboxylation by characterizing the odd versus even numbered carbons in a deoxygenated product.

Most catalysts used for performing a catalytic deoxygenation of a biocomponent feed will be less than 100% selective for a given pathway. Instead, at least some deoxygenation of a feed will typically occur via each of the three pathways mentioned above during a typical catalytic deoxygenation of a feed. The relative amounts of deoxygenation by each method will vary depending on the nature of the catalyst and the reaction conditions.

Because feeds derived from biological sources typically have carbon chains with even numbers of carbon molecules, hydrodeoxygenation can be distinguished from decarbonylation and decarboxylation based on the carbon chain length of the resulting molecules. Hydrodeoxygenation can typically lead to production of molecules with an even number of carbon atoms, while decarbonylation and decarboxylation can typically lead to molecules with an odd number of carbon atoms.

Conversion of Glycerides to Ketone-Containing Product

A catalyst suitable for partial deoxygenation and reaction of glycerides (such as triglycerides) to form ketones is a catalyst that includes a rare earth metal, such as a metal salt of a rare earth metal, an alkali metal, an alkaline earth metal, or a combination thereof. Some suitable catalysts include clay materials containing a rare earth metal, an alkali metal, and/or an alkaline earth metal. For example, hydrotalcite is a clay that includes magnesium hydroxide. Other examples of suitable catalysts include support materials impregnated with a rare earth metal salt, an alkali metal salt, and/or an alkaline earth metal salt, such as an oxide, hydroxide, or carbonate. For example, a refractory support such as titanium oxide, zirconium oxide, and/or cerium oxide can be impregnated with a lanthanum, sodium, and/or potassium salt, such as potassium carbonate. Still other examples of suitable catalysts include bulk and/or supported versions of rare earth, alkali, or alkaline earth metal salts, such as magnesium oxide and/or cesium oxide. More generally, alkali metal salts can include salts of Na, K, Rb, and/or Cs, while alkaline earth metal salts can include salts of Mg, Ca, Sr, and/or Ba. Rare earth metal salts can include, but are not limited to, salts of La, Ce, and/or Y. Thus, a reference herein to a rare earth metal or rare earth metal salt is defined to include at least La, Ce, and/or Y. The catalyst can include at least about 5 wt % of the rare earth metal salt, alkali metal salt, or alkaline earth metal salt relative to the total catalyst weight, for example at least about 15 wt % or at least about 25 wt %. For catalysts based on clays, the catalyst can include about 75 wt % or less of rare earth metal salt, alkali metal salt, or alkaline earth metal salt, for example about 50 wt % or less, about 35 wt % or less, or about 25 wt % or less. For supported catalysts, the catalyst can include about 35 wt % or less of rare earth metal salt, alkali metal salt, or alkaline earth metal salt, for example about 25 wt % or less or about 15 wt % or less. In general, higher percentages of a rare earth metal salt, an alkali metal salt, or an alkaline earth metal salt can be desirable, but practical factors may limit the amount of rare earth metal salt, alkali metal salt, and/or alkaline earth metal salt. For example, supported catalysts may be limited based on the amount of salt that can be impregnated or otherwise added to a support in a manner stable in the reaction environment. Similarly, the amount of rare earth metal salt, alkali metal salt or alkaline earth metal salt present in a clay may be limited in order to form a stable clay.

To convert glycerides (and optionally free fatty acids and/or fatty acid derivatives) to ketones, a glyceride-containing feed (or free fatty acid- and/or fatty acid derivative-containing feed) can be exposed to a catalyst containing a rare earth metal, alkali metal, and/or alkaline earth metal under effective conditions for performing a reaction to convert glycerides (and optionally free fatty acids/fatty acid derivatives) to ketones. The effective conditions for the conversion reaction can include a temperature from about 300° C. to about 450° C. It is not believed that hydrogen gas is required to facilitate the condensation reaction. However, in aspects where a single reactor is used both for forming ketones as well as deoxygenation and for isomerization of a feed, hydrogen can typically be present in order to facilitate the deoxygenation and isomerization reactions. As a result, in such embodiments, a hydrogen partial pressure of about 1.8 MPag to about 34.6 MPag can typically be present. In such a configuration, the reaction temperature can be from about 300° C. to about 450° C., for example from 320° C. to 360° C., in order to balance the benefits of the reactions occurring in the single reaction environment.

Exposure of glycerides, free fatty acids, and/or fatty acid derivatives to a rare earth, alkali metal, and/or alkaline earth metal catalyst can tend to generate a mixture of products. One of the majority products in such a mixture can generally be a fatty ketone. It is believed that fatty ketones are formed via a reaction between side chains of the glycerides and/or the chains of the free fatty acids and/or fatty acid derivatives.

FIG. 1 shows an example of a conventional reaction mechanism for conversion of a triglyceride into a fatty ketone. In FIG. 1, a triglyceride is shown as an initial starting molecule. In a conventional reaction mechanism, the triglyceride is hydrotreated, resulting in formation of three fatty acid molecules and a molecule of propane that corresponds to the three carbon backbone. Alternatively, the triglyceride can be hydrolyzed to generate three free fatty acid molecules and one glycerol molecule. The hydrolysis can be acid or base catalyzed. After separating the fatty acid molecules, such as by extraction in an organic solvent, the fatty acids can be condensed to form ketone molecules.

The rare earth, alkali, and/or alkaline earth catalysts according to the invention can allow for the direct conversion of triglycerides and other glycerides to fatty ketones, without requiring an initial step to form the free fatty acid. The addition of hydrogen and/or water to generate free fatty acids may also not be required. Instead, exposing a glyceride-containing feedstock to the rare earth, alkali, and/or alkaline earth metal can allow for direct conversion of glycerides to a mixture of ketones.

Figure 2:
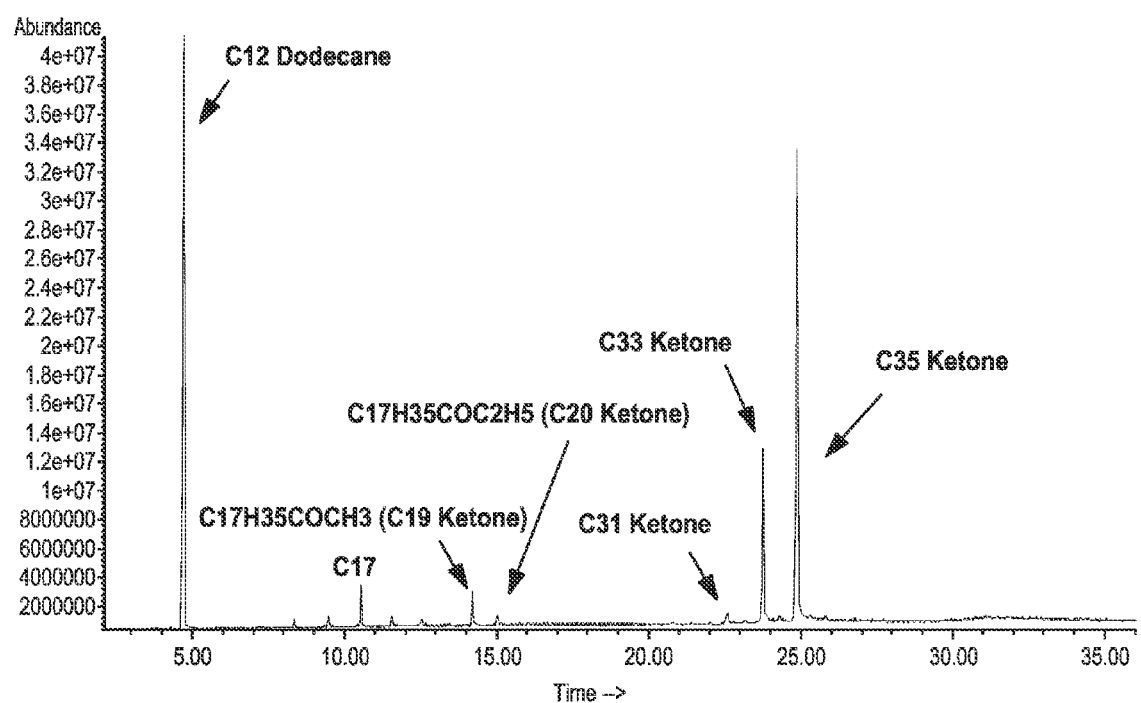
FIG. 2 shows results from processing a triglyceride-containing feed according to an aspect of the invention.

As an example, FIG. 2 shows results from reacting triglycerides over a hydrotalcite catalyst according to the invention. To generate the data shown in FIG. 2, a feed containing the triglyceride tristearin was exposed to a hydrotalcite catalyst at a temperature of about 325° C. and a hydrogen partial pressure of about 400 psig (about 2.8 MPag) in a batch environment. Although hydrogen was added to this experiment, it is believed that hydrogen is not required for ketone formation. The side chains in tristearin correspond to the fatty acid stearic acid, which is an 18-carbon saturated fatty acid. However, some side chains of other lengths were also present due to impurities in the tristearin feed. With the exception of such impurities, the feed contained approximately 100 wt % of tristearin.

FIG. 2 shows a gas chromatography-mass spectrometry (GC/MS) analysis of the reaction products formed from exposing the tristearin feed to the hydrotalcite catalyst as described above. To perform the GC/MS analysis, dodecane was added to the sample as an internal standard. As shown in FIG. 2, the primary product generated was a $C_{35}$ ketone, which corresponded to the expected ketone that would be generated by a condensation reaction between two stearic acid molecules. Although some $C_{33}$ ketone was observed, it is believed that this product was primarily due to the presence of some side chains corresponding to a 16-carbon fatty acid in the sample. The small peak observed for a $C_{31}$ ketone tends to support this interpretation. Further, it was assumed that some extent of cracking took place, which could have led to the formation of the observed shorter chain $C_{19}$ and $C_{20}$ ketones.

Based on FIG. 2, it is believed that exposing a triglyceride-containing feed (or other glyceride-containing feed) to a rare earth, alkali, and/or alkaline earth catalyst under effective conversion conditions can result in formation of ketones from the triglycerides. Also as shown in FIG. 2, to the degree that the triglyceride sample corresponds to a mixture of side chains with varying numbers of carbons and/or functional groups, the resulting ketones can also have variations in length/functionality.

In order to provide a general way of characterizing the ketones resulting from conversion of a glyceride feed, the average number of carbons (i.e., average carbon number) in ketones derived from glycerides can be compared with the average number of carbons in the side chains of the glycerides. The average number of carbons in ketones derived from glycerides in a feed can be at least about 1.5 times the average number of carbons in the side chains of the corresponding glycerides, for example at least about 1.75 times the average number of carbons in the side chains or at least about 1.9 times the average number of carbons. Because the feedstock may contain less than 100 wt % of glycerides, the amount of ketones having a specified average carbon number can be normalized by the weight percentage of glycerides in the feed. The weight of ketones in the converted effluent (prior to any deoxygenation) having a specified average number of carbons can be at least 0.5 times the weight of glycerides in the feedstock, for example at least 0.75 times the weight of glycerides in the feedstock or at least 0.9 times the weight of glycerides in the feedstock. For example, consider a feed containing 50 wt % of triglycerides with an average carbon number of 18 for the side chains. In such an example, the converted effluent can contain at least 25 wt % of ketones (at least 0.5 times the weight of triglycerides) with an average carbon number of at least 27 (at least 1.5 times the average carbon number for triglyceride side chains). Additionally or alternately, such a converted effluent could contain at least 37.5 wt % ketones (at least 0.75 times the weight of triglycerides) having an average carbon number of at least 27, and/or at least 45 wt % ketones (at least 0.9 times the weight of triglycerides) having an average carbon number of at least 27.

In some aspects, a feed may contain substantial quantities of both glycerides and free fatty acids and/or fatty acid derivatives, such as fatty acid esters and/or fatty acid amides. For example, the weight of free fatty acids and/or fatty acid derivatives in a feedstock may be at least about 10% of the combined weight of glycerides and free fatty acids and/or fatty acid derivatives, for example at least about 25% of the combined weight. In such an aspect, the ketones resulting from the conversion reaction can be characterized relative to the combined properties of the glycerides, free fatty acids, and fatty acid derivatives in the feedstock. Thus, similar to the definition above, the average carbon number of the ketones generated by the conversion reaction can be at least about 1.5 times (for example, at least about 1.75 times or at least about 1.9 times) of a weighted average based on the average number of carbons in the side chains of triglycerides and the average chain length of the free fatty acids and/or fatty acid derivatives. The weighted average can be based on the relative amounts of glycerides, free fatty acids, and/or fatty acid derivatives in the feedstock. Also in parallel to the definition above, the amount of ketones produced can be normalized by the combined weight percentage of glycerides, free fatty acids, and fatty acid derivatives in the feedstock. Thus, the amount of ketones having a specified average carbon number can be at least about 50% (for example, at least about 75% or at least about 90%) of the combined weight of glycerides, free fatty acids, and fatty acid derivatives in the feedstock.

Preferably, a catalyst selected for catalyzing the conversion of glycerides to ketones can remain relatively stable in the reaction environment. The conversion of glycerides and/or free fatty acids to ketones using a rare earth, alkali, and/or alkaline earth metal catalyst can result in some production of water, so catalysts that deteriorate in water may pose some difficulties in scaling up a process for commercial use. It is noted that the clay hydrotalcite can be effective for catalyzing the reactions described herein. However, hydrotalcite also appears to break down over time in the conditions for converting triglycerides to ketones. Without being bound by any particular theory, this may due to a phase change of the hydrotalcite alumina in the hydrothermal environment. Some phases of alumina, such as γ-alumina, are believed to be unstable in a hydrothermal processing environment, leading to phase changes for supports composed of such types of alumina that can result in a loss of activity over time. An example of a hydrothermally stable catalyst suitable for coupling of glycerides and/or free fatty acids to ketones includes, but is not limited to, lanthanum impregnated zirconia.

Isomerization of Ketone-Containing Product

After forming ketones from glycerides and optionally free fatty acids, a second catalyst can be used to deoxygenate the ketones formed from exposure to the rare earth, alkali, and/or alkaline earth metal catalyst. Preferably, the second catalyst can also be suitable for isomerizing the resulting deoxygenated molecules. An additional consideration in selecting a second catalyst can be that the catalyst should be relatively stable in the presence of water, due to the water generated during conversion of the triglycerides to ketones.

Suitable catalysts for performing deoxygenation and isomerization in an environment containing water can include dewaxing catalysts, such as zeolites, that are bound using a binder material so that the catalyst can be stable in the presence of water under effective deoxygenation conditions. Such a binder material is referred to herein as a hydrothermally stable binder. Examples of suitable dewaxing catalysts can include zeolites that perform dewaxing primarily by isomerizing a hydrocarbon feedstock. Optionally, the dewaxing catalysts can be zeolites with a unidimensional pore structure. Suitable catalysts can include 10-member ring pore zeolites, such as EU-1, ZSM-35 (or ferrierite), ZSM-11, ZSM-57, NU-87, SAPO-11, ZSM-22, and the like, as combinations thereof. Preferred materials can comprise EU-2, EU-11, ZBM-30, ZSM-48, and/or ZSM-23, with materials comprising at least ZSM-48 being particularly preferred. Note that a zeolite having the ZSM-23 structure with a silica to alumina ratio from about 20:1 to about 40:1 can sometimes be referred to as SSZ-32. Additional or alternate molecular sieves that are isostructural with the above materials can include, but are not limited to, Theta-1, NU-10, EU-13, KZ-1, NU-23, and combinations thereof.

The catalysts can optionally but preferably additionally include a metal hydrogenation component. The metal hydrogenation component can typically include a Group VI and/or a Group VIII metal. In one preferred embodiment, the metal hydrogenation component can be a Group VIII noble metal, such as Pt, Pd, or a mixture thereof. In an alternative preferred embodiment, the metal hydrogenation component can be a combination of a non-noble Group VIII metal with a Group VIB metal. Suitable combinations can include Ni, Co, and/or Fe with Mo and/or W, preferably Ni with Mo and/or W.

The metal hydrogenation component may be added to the catalyst in any convenient manner. One technique for adding the metal hydrogenation component is by incipient wetness. For example, after combining a zeolite and a hydrothermally stable binder, the combined zeolite and binder can be extruded into catalyst particles. These catalyst particles can then be exposed to a solution containing a suitable metal precursor. Additionally or alternately, metal can be added to the catalyst by ion exchange, where a metal precursor can be added to a mixture of zeolite (or zeolite and binder) prior to extrusion.

When a metal hydrogenation component is present, the amount of metal in the catalyst can be at least 0.1 wt % based on catalyst, for example at least 0.15 wt %, at least 0.2 wt %, at least 0.25 wt %, at least 0.3 wt %, or at least 0.5 wt %, based on the total weight of the catalyst. Additionally or alternately, the amount of metal in the catalyst can be 20 wt % or less based on catalyst, for example 10 wt % or less, 5 wt % or less, 2.5 wt % or less, or 1 wt % or less. For embodiments where the metal comprises Pt, Pd, another Group VIII noble metal, or a combination thereof, the amount of metal can be from 0.1 wt % to 5 wt %, for example from 0.1 to 2 wt %, from 0.25 wt % to 1.8 wt %, or from 0.4 wt % to 1.5 wt %. For embodiments where the metal comprises a combination of a non-noble Group VIII metal with a Group VIB metal, the combined amount of metal can be from 0.5 wt % to 20 wt %, for example from 1 wt % to 15 wt % or from 2.5 wt % to 10 wt %.

Preferably, the dewaxing catalysts used in processes according to the invention can exhibit a low ratio of silica to alumina. For example, for ZSM-48, the ratio of silica to alumina in the zeolite can be less than 200:1, for example less than 110:1, less than 100:1, less than 90:1, or less than 80:1. In various embodiments, the ratio of silica to alumina can be from 30:1 to 200:1, for example from 60:1 to 110:1 or from 70:1 to 100:1.

The dewaxing catalysts useful in processes according to the invention can also include a hydrothermally stable binder.

Examples of suitable hydrothermally stable binders can include metal oxides such as titanium oxides, zirconium oxides, cerium oxides, and combinations thereof. By contrast, aluminum oxides are not believed to be typically suitable for use as binders in reaction environments that contain water. Preferably, the catalyst for deoxygenation and isomerization can include a binder material that can provide enhanced activity for deoxygenation, such as a titania binder.

Optionally, the dewaxing catalysts can be formulated using a relatively low surface area binder, a relatively low surface area binder representing a binder with a surface area of 100 $m^2/g$ or less, for example 80 $m^2/g$ or less or 70 $m^2/g$ or less. Additionally or alternately, the binder and/or the zeolite particle size can be selected to provide a catalyst with a desired ratio of micropore surface area to total surface area. In dewaxing catalysts used according to the invention, the micropore surface area corresponds to surface area from the unidimensional pores of zeolites in the dewaxing catalyst. The total surface corresponds to the micropore surface area plus the external surface area. Any binder used in the catalyst will typically not contribute much to the micropore surface area and typically will not significantly increase the total surface area of the catalyst. The external surface area represents the balance of the surface area of the total catalyst minus the micropore surface area. Both the binder and zeolite can contribute to the value of the external surface area. Preferably, the ratio of micropore surface area to total surface area for a dewaxing catalyst can be equal to or greater than 25%.

A zeolite can be combined with binder in any convenient manner. For example, a bound catalyst can be produced by starting with powders of both the zeolite and binder, combining and mulling the powders with added water to form a mixture, and then extruding the mixture to produce a bound catalyst of a desired size. Extrusion aids can optionally be used to modify the extrusion flow properties of the zeolite and binder mixture.

In some embodiments, a binder composed of two or more metal oxides can be used. In such embodiments, the weight percentage of the low surface area binder can preferably be greater than the weight percentage of the higher surface area binder. Alternatively, if both metal oxides used for forming a mixed metal oxide binder have a sufficiently low surface area, the proportions of each metal oxide in the binder can be less important. When two or more metal oxides are used to form a binder, the two metal oxides can be incorporated into the catalyst by any convenient method. For example, one binder can be mixed with the zeolite during formation of the zeolite powder, such as during spray drying. The spray dried zeolite/binder powder can then be mixed with the second metal oxide binder prior to extrusion.

Process conditions for catalytic dewaxing can include at least one of: a temperature from 200° C. to 450° C., for example from 270° C. to 400° C.; a hydrogen partial pressure from 1.7 MPag (250 psig) to 34.5 MPag (5000 psig), for example from 4.8 MPag (700 psig) to 20.7 MPag (3000 psig); a liquid hourly space velocity (LHSV) from 0.2 v/v/hr to 10 v/v/hr, for example from 0.5 v/v/hr to 3.0 v/v/hr; and a hydrogen circulation rate from 35.6 $Nm^3/m^3$ (200 scf/B) to 1780 $Nm^3/m^3$ (10,000 scf/B), for example from 178 $Nm^3/m^3$ (1000 scf/B) to 891 $Nm^3/m^3$ (5000 scf/B).

There are several alternatives for how to incorporate the dewaxing catalyst in the reaction system. One option can be to configure the rare earth, alkali, and/or alkaline earth metal catalyst and the dewaxing catalyst as stacked beds. In this type of configuration, a reactor or reaction system can contain one or more initial beds of a rare earth, alkali, and/or alkaline earth metal catalyst for converting triglycerides to ketones. As described above, exposing a glyceride-containing feed to the one or more initial beds of rare earth, alkali, and/or alkaline earth metal catalyst can result in production of an effluent containing ketones based on the side chains in the glycerides. The effluent containing ketones can then be exposed to one or more beds of a dewaxing catalyst under effective dewaxing conditions. This can result in deoxygenation of the ketone-containing effluent. Additionally, the dewaxing catalyst can introduce branches into (isomerize) the carbon chains of the ketones (or deoxygenated ketones). For glycerides with side chains that originally contain only carbon, hydrogen, and oxygen, the combination of forming ketones, deoxygenation, and isomerization can result in branched hydrocarbons containing one or more branches, such as methyl branches. Of course, if the side chains of the triglycerides contain other types of heteroatoms, such as nitrogen and/or sulfur, other types of molecules may be generated.

For glycerides with side chains containing between 12 and 20 carbon atoms (or free fatty acids/fatty acid derivatives with 12-20 carbon atom chains), the stacked bed configuration of rare earth, alkali, and/or alkaline earth metal catalyst and dewaxing catalyst can result in production of deoxygenated molecules that can advantageously boil in the lubricant boiling range as a primary product, with some production of deoxygenated molecules that can boil in the diesel boiling range. The lubricant boiling range molecules can correspond to ketones that were formed during conversion of the glycerides (and/or free fatty acids) in the feedstock. These ketones can subsequently be deoxygenated and isomerized. However, while the process of converting glycerides to fatty acids can typically occur at approximately 100% conversion, less than all of the side chains in the glycerides (and/or free fatty acids) may result in formation of ketones. Instead, at least a portion of the side chains from the glycerides can reach the dewaxing catalyst without combining with another side chain to form a lubricant boiling range molecule. These uncombined side chains can also be deoxygenated and isomerized by the dewaxing catalyst, resulting in diesel boiling range molecules. Thus, a stacked bed arrangement for the catalysts would be expected to generate a majority portion of lubricant boiling range molecules from a triglyceride feed and a minority portion of diesel boiling range molecules.

An alternative configuration can be to combine both the rare earth/alkali/alkaline earth metal catalyst and the dewaxing catalyst in the same catalyst bed. In this type of configuration, both the rare earth/alkali/alkaline earth metal catalyst and the dewaxing catalyst can be exposed to the initial feed. In this type of configuration, an increased amount of the initial glycerides (and/or free fatty acids) in the feed can be converted to diesel boiling range molecules. This is believed to be due to the ability of the dewaxing catalyst to deoxygenate the side chains of the glycerides (and/or of an intermediate product of the glycerides, such as fatty acids) before reaction to form a ketone can occur.

By blending varying amounts of dewaxing catalyst and rare earth/alkali/alkaline earth metal in a combined catalyst bed, the ratio of the amount of diesel boiling range molecules versus lubricant boiling range molecules can be adjusted. Thus, still another option can be to use "stacked" beds of various mixtures of the rare earth, alkali, and/or alkaline earth metal catalyst and the dewaxing catalyst. For example, a catalyst bed or beds containing 80% of a rare earth, alkali, and/or alkaline earth metal catalyst and 20% of a dewaxing catalyst can produce a larger amount of lubricant boiling range molecules than a catalyst bed or beds containing 25% of the rare earth, alkali, and/or alkaline earth metal catalyst and 75% of the dewaxing catalyst. An additional or alternate option for controlling the relative amounts of lubricant and diesel boiling range molecules can be to combine the stacked bed and mixed bed concepts. For example, an initial bed or an initial portion of a catalyst bed can correspond to a rare earth, alkali, and/or alkaline earth metal catalyst, a second bed or bed portion can correspond to a mixture of catalysts, and a third bed or portion can correspond to a dewaxing catalyst. Still other options for setting up various types of gradients in the amount of rare earth, alkali, and/or alkaline earth metal catalyst and dewaxing catalyst can additionally or alternately be used.

In order to provide a general way of characterizing the hydrocarbons resulting from conversion, deoxygenation, and isomerization of a glyceride feed, the average carbon number in deoxygenated molecules derived from glycerides can be compared with the average number of carbons in the side chains of the glycerides. The average number of carbons in deoxygenated molecules derived from glycerides in a feed can be at least about 1.5 times the average number of carbons in the side chains of the corresponding glycerides, for example at least about 1.75 time the average number of carbons in the side chains or at least about 1.9 times the average number of carbons. If the weight of free fatty acids and fatty acid derivatives corresponds to more than about 10 wt % of the combined weight of glycerides, free fatty acids, and fatty acid derivatives, for example at least about 25 wt %, the average number of carbons in deoxygenated molecules can instead be compared with weighted average number of carbons in the combined glycerides, free fatty acids, and fatty acid derivatives in the feedstock.

Due to the ability of methods according to various aspects to perform a conversion to ketones starting with a glyceride feed, it can be preferable for a feed including both glycerides and free fatty acids and/or fatty acid derivatives to contain at least 10 wt % of glycerides, for example at least 25 wt % of glycerides. Optionally but preferably, a feed including both glycerides and free fatty acids and/or fatty acid derivatives can have a weight percentage of glycerides greater than the combined weight percentage of free fatty acids and fatty acid derivatives.

Because the feedstock may contain less than 100 wt % of glycerides (or less than 100 wt % of glycerides and free fatty acids), the amount of deoxygenated molecules having a specified average carbon number can be normalized by the weight percentage of glycerides (or combined weight percentage of glycerides, free fatty acids, and fatty acid derivatives) in the feed. In a situation where coupling to form ketones and deoxygenation/isomerization is performed sequentially using stacked beds, the weight of deoxygenated molecules in the product effluent having a specified average number of carbons can be at least 0.5 times the weight of glycerides (and/or glycerides and free fatty acids) in the feedstock, for example at least 0.75 times the weight or at least 0.9 times the weight. As above, the combined weight of glycerides, free fatty acids, and fatty acid derivatives can be used in situations where the amount of free fatty acids and/or fatty acid derivatives in the feed is at least about 10 wt % of the combined weight of glycerides and free fatty acids, for example at least about 25 wt %. As an example, consider a feed containing 50 wt % of triglycerides with an average carbon number of 18 for the side chains. In such an example, the converted effluent can contain at least 25 wt % of ketones (at least 0.5 times the weight of triglycerides) with an average carbon number of at least 27 (at least 1.5 times the average carbon number for triglyceride side chains). Additionally or alternately, such a converted effluent could contain at least 37.5 wt % ketones (at least 0.75 times the weight of triglycerides) having an average carbon number of at least 27, and/or at least 45 wt % ketones (at least 0.9 times the weight of triglycerides) having an average carbon number of at least 27.

As an alternative, mixed beds of conversion catalyst and deoxygenation/isomerization catalyst may be used. As noted above, in this configuration at least a portion of the glyceride side chains and/or free fatty acid chains may contact the deoxygenation/isomerization catalyst prior to coupling to form a ketone. This can result in production of a higher percentage of diesel boiling range molecules in place of lubricant boiling range molecules. As a result, when mixed catalyst beds are used, the weight of deoxygenated molecules in the product effluent having a specified average number of carbons can be at least 0.1 times the weight of glycerides (or glycerides, free fatty acids, and fatty acid derivatives) in the feedstock, for example at least 0.2 times the weight, at least 0.25 times the weight, or at least 0.5 times the weight.

Configurations for Formation of Distillate Products

Figure 3:
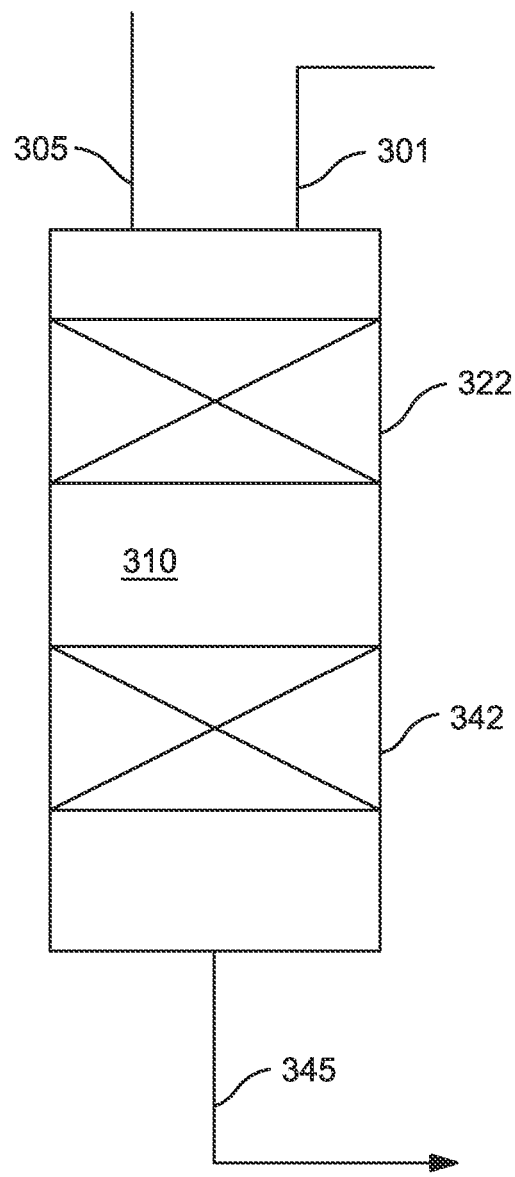
FIG. 3 schematically shows a reaction system suitable for performing a process according to an aspect of the invention.

FIG. 3 shows an example of a reactor suitable for processing a glyceride- and/or free fatty acid-containing feed. In FIG. 3, reactor 310 is shown as containing reaction zones 322 and 342. Each reaction zone can correspond to one or more catalyst beds. Alternatively, one or more reactors may be used in a cascade configuration, and any convenient number of reaction zones may be used within a reactor.

In stacked bed configuration, reaction zone 322 can contain one or more catalyst beds of a rare earth, alkali, and/or alkaline earth metal catalyst. A glyceride-containing feedstock 305 is introduced into reactor 310 so that the feedstock is exposed to the catalyst in the catalyst beds in reaction zone 322 prior to being exposed to the catalyst in reaction zone 342. Optionally, the feedstock 305 can include both glycerides and free fatty acids. In FIG. 3, hydrogen treat gas 301 is shown as entering reactor 310 in a co-current manner relative to the flow of the feedstock 305. Alternatively, hydrogen treat gas can be introduced into reactor 310 in other convenient manners, such as introducing the hydrogen treat gas to flow counter-current relative to feedstock 305.

After passing through reaction zone 322, the effluent is exposed to the catalyst in the one or more catalyst beds in reaction zone 342. Depending on the configuration, reaction zone 342 is an optional reaction zone. For example, in a configuration where only mixed beds of catalyst are used, only a single reaction zone 322 may be needed. The effluent from reaction zone 342 (or optionally reaction zone 322) then exits the reactor as a product effluent flow 345.

In one type of stacked bed configuration, the one or more catalyst beds in reaction zone 322 correspond to a rare earth, alkali, and/or alkaline earth metal catalyst, while the one or more catalyst beds in reaction zone 342 correspond to a dewaxing catalyst. In another type of stacked bed configuration, one or both of reaction zones 322 and 342 can contain mixed beds of rare earth, alkali, and/or alkaline earth metal catalyst and dewaxing catalyst. In this type of configuration, the volume percentage of the dewaxing catalyst is greater in the catalyst beds in reaction zone 342 as compared to the volume percentage of dewaxing catalyst in the catalyst beds in reaction zone 322. In various stacked bed configurations, the effluent from reaction zone 322 can be passed into reaction zone 342 without intermediate separation. In such a configuration, any gas phase products generated during processing in reaction zone 322, such as water vapor generated by coupling reactions for the formation of ketones, will be passed into reaction zone 342 along with the liquid effluent.

Still another option is to have a uniform mixture of dewaxing catalyst and rare earth, alkali, and/or alkaline earth metal catalyst within the reaction zones in the reactor. In this type of configuration, reaction zone 342 is optional, as the same or similar conditions are present throughout the reactor. Thus, all catalyst beds within the reactor can alternatively be thought of as being in reaction zone 322.

Example of Processing Triglycerides

Figure 4:
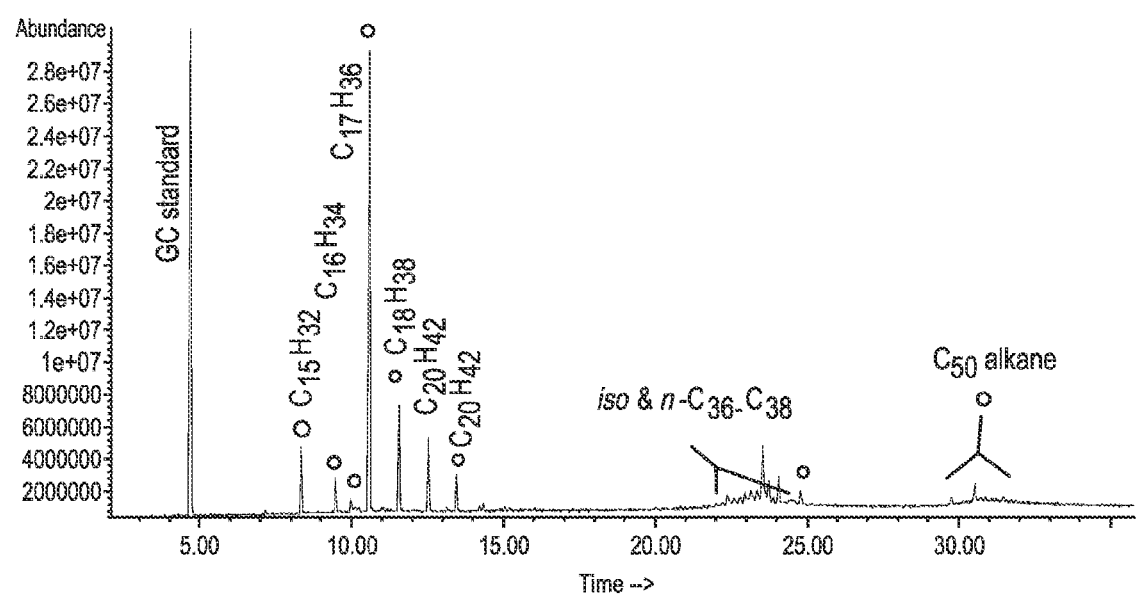
FIG. 4 shows results from processing a triglyceride-containing feed according to an aspect of the invention.

FIG. 4 shows results from the processing of a triglyceride-containing feed by exposing the feed to a mixed bed of an alkaline earth metal catalyst and a dewaxing catalyst. In this example, tristearin was exposed to a mixed catalyst bed that contained equal volumes of an alkaline earth metal catalyst and a dewaxing catalyst in a batch reaction environment. The alkaline earth metal catalyst was hydrotalcite. The dewaxing catalyst was ZSM-48 catalyst bound with $TiO_2$. The catalyst was impregnated with about 0.6 wt % of Pt as a hydrogenation metal. The tristearin feed was exposed to the mixed catalyst bed at a temperature of about 325° C. and a hydrogen partial pressure of about 400 psig (about 2.8 MPag).

FIG. 4 shows a GC/MS analysis of the reaction products generated during the reaction. In FIG. 4, the listing of components in the reaction products corresponds to the order of the appearance of the products from left to right. Thus, the left most identified product in FIG. 4 is pentadecane. As shown in FIG. 4, the majority of the product generated from the tristearin was n-heptadecane, a $C_{17}$ linear paraffin. This corresponded to the expected product if a decarbonylation or decarboxylation reaction was performed on stearic acid, a $C_{1-8}$ saturated carboxylic acid. The second most common product was octadecane, which corresponded to the expected product from hydrodeoxygenation of stearic acid. Some $C_{32}$-$C_{36}$ paraffins were also formed, indicating some formation of a ketone corresponding to multiple side chains. This is the reaction product that would have been expected from a stacked bed arrangement of the hydrotalcite and ZSM-48 catalysts. A small amount of $C_{36}$ ketone was also present in the reaction products, indicating incomplete deoxygenation of ketones formed by exposure of the tristearin to the hydrotalcite catalyst.

Based on FIG. 4, processing of the triglycerides in tristearin over a mixed bed of hydrotalcite and a ZSM-48 dewaxing catalyst resulted in production of about 75-80% diesel boiling range molecules and about 20-25% of lubricant boiling range molecules, with a portion of the lubricant boiling range molecules corresponding to unreacted ketone. The unreacted ketone could be removed by following a mixed catalyst bed with a short additional bed of dewaxing catalyst.

In contrast to FIG. 4, FIG. 2 shows the results from processing of the tristearin feed over a bed of only hydrotalcite. In FIG. 2, about 80% of the molecules corresponded to lubricant boiling range molecules in the form of ketones, and about 20% of the molecules corresponded to diesel boiling range ketones/paraffins. In a stacked bed configuration, the effluent from a hydrotalcite or other rare earth/alkali/alkaline earth metal catalyst can be exposed to a dewaxing catalyst. This would be expected to result in an approximately 80% lubricant boiling range molecules and 20% diesel boiling range molecules.

In still other configurations, other percentages of diesel and boiling range molecules can be achieved based on a glyceride feed (and/or glyceride/free fatty acid/fatty acid derivative feed). For example, modifying the ratio of rare earth, alkali, and/or alkaline earth metal catalyst and dewaxing catalyst in a mixed bed can allow for variation of the relative amounts of diesel and lubricant boiling range molecules. Similarly, using shorter or longer beds of the rare earth/alkali/alkaline earth metal catalyst could alter the amount of ketones formed by the rare earth/alkali/alkaline earth metal catalyst prior to exposing the feed to the dewaxing catalyst. One practical limitation on the types of configurations can be the constraint of achieving a sufficiently complete reaction. For example, it can typically be preferred to reduce the oxygen content of the feed to less than 1 wt %, for example to less than about 0.5 wt % or less than about 0.25 wt %. Reducing the oxygen concentration to these levels can typically allow a feed to be processed in other types of reactors in a refinery. Thus, it can be preferable to have sufficient amounts of dewaxing catalyst toward the end of the reaction zones or catalyst beds, so that the resulting product effluent can be sufficiently deoxygenated. Furthermore, the rare earth, alkali, and/or alkaline earth metal catalyst is believed to have greater activity for converting triglycerides (and/or other glycerides) in a feedstock to other forms. Thus, it can be preferable to have sufficient amounts of a rare earth, alkali, and/or alkaline earth metal catalyst in the early portions of the reaction zones or catalyst beds to facilitate conversion of the glycerides.

ADDITIONAL EMBODIMENTS

Embodiment 1

A method for processing a glyceride-containing feedstock, comprising: exposing a feedstock containing glycerides (e.g., at least 10 wt % glycerides, at least 25 wt % glycerides, or at least 50 wt % glycerides) to a catalyst comprising at least about 5 wt % of a rare earth metal salt, an alkali metal salt, an alkaline earth metal salt, or a combination thereof in the presence of hydrogen under effective deoxygenation conditions to form an effluent containing ketones, the weight percentage of ketones in the effluent being at least about 50% of the weight percentage (e.g., about 75% of the weight percentage or about 90% of the weight percentage) of the glycerides in the feedstock; and exposing, without intermediate separation, at least a portion of the effluent containing ketones to a dewaxing catalyst bound with a hydrothermally stable binder under effective dewaxing conditions to form a deoxygenated effluent, wherein the glycerides in the feedstock have an average carbon number for side chains in the glycerides, and wherein an average carbon number of the ketones in the effluent is greater than 1.5 times (e.g., greater than 1.75 times or greater than 1.9 times) the average carbon number for the side chains.

Embodiment 2

The method of Embodiment 1, further comprising fractionating the deoxygenated effluent to form at least a diesel boiling range fraction and a lubricant boiling range fraction.

Embodiment 3

The method of any of the above embodiments, wherein the feedstock further comprises at least one of free fatty acids and fatty acid derivatives, the fatty acid derivatives being fatty acid esters, fatty acid amides, or a combination thereof.

Embodiment 4

The method of Embodiment 3, wherein the weight percentage of ketones in the effluent containing ketones is at least about 50% of the combined weight percentage (e.g., about 75% of the weight percentage or about 90% of the weight percentage) of the glycerides, free fatty acids, and fatty acid derivatives in the feedstock, the free fatty acids and fatty acid derivatives in the feedstock having an average carbon number for the fatty acid chains, and wherein the average carbon number of the ketones in the effluent is greater than 1.5 times (e.g., greater than 1.75 times or greater than 1.9 times) the weighted average carbon number for the side chains of the glycerides and the fatty acid chains of the free fatty acids and fatty acid derivatives.

Embodiment 5

A method for processing a glyceride-containing feedstock, comprising: exposing a feedstock containing at least 10 wt % glycerides (e.g., at least 25 wt % glycerides or at least 50 wt % glycerides) to a catalyst mixture comprising a dewaxing catalyst bound with a hydrothermally stable binder and a catalyst comprising at least about 5 wt % of a rare earth metal salt, alkali metal salt, alkaline earth metal salt, or a combination thereof in the presence of hydrogen under effective deoxygenation conditions, the effective deoxygenation conditions including a temperature of at least about 300° C., to form a deoxygenated effluent, wherein the glycerides in the feedstock have an average carbon number for side chains in the glycerides, and at least 1 wt % (e.g., at least 5 wt % or at least 25 wt %) of the deoxygenated effluent comprises lubricant boiling range molecules derived from the glycerides in the feedstock, the lubricant boiling range molecules having a number of carbon atoms greater than 1.5 times (e.g., greater than 1.75 times or greater than 1.9 times) the average carbon number for the glyceride side chains.

Embodiment 6

The method of Embodiment 5, wherein exposing the feedstock to a catalyst mixture comprises exposing the feedstock to a plurality of mixed catalyst beds, wherein a catalyst mixture in a first mixed catalyst bed has a lower volume percentage of dewaxing catalyst than a second mixed catalyst bed that is downstream relative to the flow of feedstock from the first mixed catalyst bed.

Embodiment 7

The method of Embodiment 5 or Embodiment 6, wherein the feedstock further comprises at least one of free fatty acids or fatty acid derivatives, the fatty acid derivatives being fatty acid esters, fatty acid amides, or a combination thereof.

Embodiment 8

The method of any of Embodiments 3, 4, or 7, wherein the combined weight of glycerides, free fatty acids, and fatty acid derivatives is at least about 10 wt % of the feedstock (e.g., at least about 25 wt % of the feedstock or at least 50 wt % of the feedstock), and at least 1 wt % (e.g., at least 5 wt % or at least 25 wt %) of the deoxygenated effluent comprises lubricant boiling range molecules derived from the glycerides, free fatty acids, and fatty acid derivatives in the feedstock, the lubricant boiling range molecules having a number of carbon atoms greater than 1.5 times (e.g., greater than 1.75 times or greater than 1.9 times) the weighted average carbon number for the side chains of the glycerides and the fatty acid chains of the free fatty acids and fatty acid derivatives.

Embodiment 9

The method of any of the previous Embodiments, wherein the dewaxing catalyst comprises ZSM-48, ZSM-23, or a combination thereof, and wherein the hydrothermally stable binder comprises titanium oxide, zirconium oxide, cerium oxide, or a combination thereof.

Embodiment 10

A method for processing a glyceride-containing feedstock, comprising: exposing a glyceride-containing feedstock containing at least 25 wt % (e.g., at least 50 wt %) of a combined weight of glycerides, free fatty acids, and fatty acid derivatives to a catalyst mixture in the presence of hydrogen under effective deoxygenation conditions to form a deoxygenated effluent, the effective deoxygenation conditions including a temperature of at least about 300° C., the fatty acid derivatives being fatty acid esters and/or fatty acid amides, the catalyst mixture comprising (a) a dewaxing catalyst comprising ZSM-48, ZSM-23, or a combination thereof, the dewaxing catalyst being bound with a hydrothermally stable binder comprising zirconium oxide, titanium oxide, cerium oxide, or a combination thereof, and (b) a catalyst comprising at least about 5 wt % of a rare earth metal salt, alkali metal salt, alkaline earth metal salt, or a combination thereof on a support comprising zirconium oxide, titanium oxide, cerium oxide, or a combination thereof, wherein the glycerides, free fatty acids, and fatty acid derivatives in the feedstock have a weighted average carbon number for the fatty acid chains and the side chains in the glycerides, and at least 1 wt % (e.g., at least 5 wt % or at least 25 wt %) of the deoxygenated effluent comprises lubricant boiling range molecules derived from the free fatty acids, fatty acid derivatives, and side chains of glycerides in the feedstock, the lubricant boiling range molecules having an average number of carbon atoms greater than 1.5 times (e.g., greater than 1.75 times or greater than 1.9 times) the weighted average carbon number for the side chains of the glycerides and the fatty acid chains of the free fatty acids and fatty acid derivatives.

Embodiment 11

The method of Embodiment 9, wherein the feedstock contains at least 10 wt % of glycerides.

Embodiment 12

The method of any of the previous Embodiments, wherein the catalyst comprising a rare earth metal salt, an alkali metal salt, an alkaline earth metal salt, or a combination thereof comprises a clay containing at least one of a rare earth metal salt, an alkali metal salt, and an alkaline earth metal salt.

Embodiment 13

The method of any of the previous Embodiments, wherein one or more of the following are satisfied: the rare earth metal salt, alkali metal salt, and/or alkaline earth metal salt is Na, K, Rb, Cs, Mg, Ca, Sr, Ba, La, Ce, Y, or a combination thereof, e.g., is Na, K, Cs, Mg, Ca, La, or a combination thereof; the catalyst further comprises a hydrothermally stable support comprising titanium oxide, zirconium oxide, cerium oxide, or a combination thereof; e.g., comprising titanium oxide and/or zirconium oxide; and the hydrothermally stable binder comprises titanium oxide.

Embodiment 14

The method of any of the previous Embodiments, wherein the glycerides in the feedstock comprise triglycerides.

What is claimed is:

1. A method for processing a glyceride-containing feedstock, comprising:
   exposing a feedstock containing at least 10 wt % glycerides to a catalyst mixture comprising a dewaxing catalyst bound with a hydrothermally stable binder and a catalyst comprising at least about 5 wt % of a rare earth metal salt, alkali metal salt, alkaline earth metal salt, or a combination thereof in the presence of hydrogen under effective deoxygenation conditions, the effective deoxygenation conditions including a temperature of at least about 300° C., to form a deoxygenated effluent,
   wherein the glycerides in the feedstock have an average carbon number for side chains in the glycerides, and at least 1 wt % of the deoxygenated effluent comprises lubricant boiling range molecules derived from the glycerides in the feedstock, the lubricant boiling range molecules having a number of carbon atoms greater than 1.5 times the average carbon number for the glyceride side chains, wherein exposing the feedstock to a catalyst mixture comprises exposing the feedstock to a plurality of mixed catalyst beds, and wherein a catalyst mixture in a first mixed catalyst bed has a lower volume percentage of dewaxing catalyst than a second mixed catalyst bed that is downstream relative to the flow of feedstock from the first mixed catalyst bed.

2. The method of claim 1, wherein the feedstock comprises at least 25 wt % of glycerides and at least 5 wt % of the deoxygenated effluent comprises lubricant boiling range molecules derived from the glycerides in the feedstock, the lubricant boiling range molecules having a number of carbon atoms greater than 1.5 times the average carbon number for the side chains.

3. The method of claim 1, wherein the feedstock comprises at least 50 wt % of glycerides and at least 25 wt % of the deoxygenated effluent comprises lubricant boiling range molecules derived from the glycerides in the feedstock, the lubricant boiling range molecules having a number of carbon atoms greater than 1.5 times the average carbon number for the side chains.

4. The method of claim 1, wherein the catalyst mixture comprises a) a dewaxing catalyst comprising ZSM-48, ZSM-23, or a combination thereof, the dewaxing catalyst being bound with a hydrothermally stable binder comprising zirconium oxide, titanium oxide, cerium oxide, or a combination thereof, and b) a catalyst comprising at least about 5 wt % of a rare earth metal salt, alkali metal salt, alkaline earth metal salt, or a combination thereof on a hydrothermally stable support comprising zirconium oxide, titanium oxide, cerium oxide, or a combination thereof.

5. The method of claim 4, wherein the rare earth metal salt, alkali metal salt, and/or alkaline earth metal salt is Na, K, Cs, Mg, Ca, La, or a combination thereof, the hydrothermally stable support comprises titanium oxide, zirconium oxide, cerium oxide, or a combination thereof, and the hydrothermally stable binder comprises titanium oxide.

6. The method of claim 1, wherein the glycerides in the feedstock comprise triglycerides.

7. The method of claim 1, wherein the feedstock further comprises at least one of free fatty acids and fatty acid derivatives, the fatty acid derivatives being fatty acid esters, fatty acid amides, or a combination thereof.

8. The method of claim 7, wherein the combined weight of glycerides, free fatty acids, and fatty acid derivatives is at least about 25 wt % of the feedstock, and at least 5 wt % of the deoxygenated effluent comprises lubricant boiling range molecules derived from the glycerides, free fatty acids, and fatty acid derivatives in the feedstock, the lubricant boiling range molecules having a number of carbon atoms greater than 1.5 times the weighted average carbon number for the side chains of the glycerides and the fatty acid chains of the free fatty acids and fatty acid derivatives.

9. A method for processing a glyceride-containing feedstock, comprising:

exposing a glyceride-containing feedstock containing at least 25 wt % of a combined weight of glycerides, free fatty acids, and fatty acid derivatives to a catalyst mixture in the presence of hydrogen under effective deoxygenation conditions to form a deoxygenated effluent, the effective deoxygenation conditions including a temperature of at least about 300° C., the fatty acid derivatives being fatty acid esters and/or fatty acid amides, the catalyst mixture comprising a) a dewaxing catalyst comprising ZSM-48, ZSM-23, or a combination thereof, the dewaxing catalyst being bound with a hydrothermally stable binder comprising zirconium oxide, titanium oxide, cerium oxide, or a combination thereof, and b) a catalyst comprising at least about 5 wt % of a rare earth metal salt, alkali metal salt, alkaline earth metal salt, or a combination thereof on a support comprising zirconium oxide, titanium oxide, cerium oxide, or a combination thereof, wherein the glycerides, free fatty acids, and fatty acid derivatives in the feedstock have a weighted average carbon number for the fatty acid chains and the side chains in the glycerides, and at least 1 wt % of the deoxygenated effluent comprises lubricant boiling range molecules derived from the free fatty acids, fatty acid derivatives, and side chains of glycerides in the feedstock, the lubricant boiling range molecules having an average number of carbon atoms greater than 1.5 times the weighted average carbon number for the side chains of the glycerides and the fatty acid chains of the free fatty acids and fatty acid derivatives, wherein exposing the glyceride-containing feedstock to a catalyst mixture comprises exposing the feedstock to a plurality of mixed catalyst beds, and wherein a catalyst mixture in a first mixed catalyst bed has a lower volume percentage of dewaxing catalyst than a second mixed catalyst bed that is downstream relative to the flow of feedstock from the first mixed catalyst bed.

10. The method of claim 9, wherein the feedstock contains at least 10 wt % of glycerides.

\* \* \* \* \*